(12) United States Patent
Reyes et al.

(10) Patent No.: US 11,653,841 B2
(45) Date of Patent: May 23, 2023

(54) MAP ESTIMATION ON VAD PATIENTS

(71) Applicant: HeartWare, Inc., Miami Lakes, FL (US)

(72) Inventors: Carlos Reyes, Davie, FL (US); Fernando Casas, Miami Lakes, FL (US)

(73) Assignee: HeartWare, Inc., Miami Lakes, FL (US)

( * ) Notice: Subject to any disclaimer, the term of this patent is extended or adjusted under 35 U.S.C. 154(b) by 895 days.

(21) Appl. No.: 16/573,011

(22) Filed: Sep. 17, 2019

(65) Prior Publication Data

US 2020/0101209 A1 Apr. 2, 2020

Related U.S. Application Data

(60) Provisional application No. 62/737,244, filed on Sep. 27, 2018.

(51) Int. Cl.
*A61B 5/021* (2006.01)
*A61B 5/00* (2006.01)
(Continued)

(52) U.S. Cl.
CPC .......... *A61B 5/02108* (2013.01); *A61B 5/746* (2013.01); *A61M 60/178* (2021.01);
(Continued)

(58) Field of Classification Search
CPC ... A61B 5/02108; A61B 5/746; A61B 5/0215; A61B 5/686; A61B 60/422;
(Continued)

(56) References Cited

U.S. PATENT DOCUMENTS 6,471,656 B1 10/2002 Shalman et al.
7,520,850 B2 * 4/2009 Brockway ........... A61M 60/523
600/17

(Continued)

FOREIGN PATENT DOCUMENTS

WO 2015179921 A1 12/2015
WO WO-2015179921 A1 * 12/2015 .......... A61M 60/148
WO WO-2016089693 A1 * 6/2016 .......... A61B 5/0215

OTHER PUBLICATIONS

International Search Report and Written Opinion dated Dec. 19, 2019, for corresponding International Application No. PCT/US2019/051417; International Filing Date: Sep. 17, 2019 consisting of 9-pages.

(Continued)

*Primary Examiner* — Susan S Su
*Assistant Examiner* — Eric Rassavong
(74) *Attorney, Agent, or Firm* — Shumaker & Sieffert, P.A.

(57) ABSTRACT

A method of determining a mean arterial pressure index of a patient having an implantable blood pump including determining a pump speed and a pump flow value; analyzing the pump speed and the pump flow value to a pump loss constant value; determining a graft hydraulic resistance value during a systolic phase of a cardiac cycle based on the analysis of the pump speed and the pump flow value to the pump loss constant value; determining a mean arterial pressure index during a diastolic phase of the cardiac cycle based on the determined graft hydraulic resistance value; comparing the mean arterial pressure index of the patient to a mean arterial pressure index range; and generating an alert when the mean arterial pressure index varies with respect to a mean arterial pressure index range.

20 Claims, 5 Drawing Sheets

(51) Int. Cl.
*A61M 60/178* (2021.01)
*A61M 60/411* (2021.01)
*A61M 60/232* (2021.01)
*A61M 60/538* (2021.01)
*A61M 60/523* (2021.01)
*A61M 60/531* (2021.01)
*A61M 60/585* (2021.01)

(52) U.S. Cl.
CPC ........ *A61M 60/232* (2021.01); *A61M 60/411* (2021.01); *A61M 60/523* (2021.01); *A61M 60/531* (2021.01); *A61M 60/538* (2021.01); *A61M 60/585* (2021.01); *A61M 2205/04* (2013.01); *A61M 2205/18* (2013.01); *A61M 2205/3334* (2013.01)

(58) Field of Classification Search
CPC .. A61B 60/554; A61B 60/857; A61M 60/178; A61M 60/232; A61M 60/411; A61M 60/523; A61M 60/531; A61M 60/538; A61M 60/585; A61M 2205/04; A61M 2205/18; A61M 2205/3334
See application file for complete search history.

(56) References Cited

U.S. PATENT DOCUMENTS

| | | | |
|---|---|---|---|
| 7,963,905 B2 | 6/2011 | Salmonsen et al. | |
| 7,997,854 B2 | 8/2011 | LaRose et al. | |
| 8,512,013 B2 | 8/2013 | Larose et al. | |
| 8,657,733 B2 * | 2/2014 | Ayre | A61B 5/686 600/17 |
| 8,974,394 B2 | 3/2015 | Frinak et al. | |
| 10,960,118 B2 * | 3/2021 | Sunagawa | A61B 5/4836 |
| 11,045,640 B2 * | 6/2021 | Ochsner | A61M 60/857 |
| 2003/0045772 A1 * | 3/2003 | Reich | A61M 60/216 600/18 |
| 2006/0167334 A1 * | 7/2006 | Anstadt | A61M 60/191 600/17 |
| 2008/0097226 A1 * | 4/2008 | McConnell | A61M 60/515 600/16 |
| 2012/0029408 A1 * | 2/2012 | Beaudin | A61M 1/369 604/4.01 |
| 2012/0245681 A1 | 9/2012 | Casas et al. | |
| 2014/0024954 A1 | 1/2014 | Frinak et al. | |
| 2014/0100413 A1 | 4/2014 | Casas et al. | |
| 2014/0200391 A1 | 7/2014 | Simons | |
| 2014/0357937 A1 | 12/2014 | Reyes et al. | |
| 2016/0166211 A1 | 6/2016 | Brown et al. | |
| 2017/0165407 A1 | 6/2017 | Farnan | |
| 2017/0185054 A1 | 6/2017 | Rudser | |
| 2017/0239407 A1 | 8/2017 | Hayward | |
| 2018/0064860 A1 * | 3/2018 | Nunez | A61M 60/816 |
| 2018/0078159 A1 * | 3/2018 | Edelman | A61B 5/02158 |
| 2018/0085507 A1 | 3/2018 | Casas et al. | |
| 2018/0147333 A1 * | 5/2018 | Rudser | A61M 60/515 |
| 2018/0280601 A1 * | 10/2018 | Harjes | A61M 60/531 |
| 2018/0337020 A1 | 11/2018 | Bishop | |

OTHER PUBLICATIONS

D. Vickers, et al., Estimation of systemic blood pressure from pump parameters in continuous-flow left ventricular assist devices, St. Vincent's Hospital, Sydney, Australia, http://dx.doi.org/10.1016/j.hlc.2015.06.224.

Kei Woldendorp, et al., A novel method of blood pressure measurement in patients with continuous-flow left ventricular assist devices, The Journal of Heart and Lung Transplantation, vol. 33, No. 11, Nov. 2014, 4 pages.

* cited by examiner

MAP ESTIMATION ON VAD PATIENTS

CROSS-REFERENCE TO RELATED APPLICATION

This application claims the benefit of U.S. Application Ser. No. 62/737,244, filed Sep. 27, 2018.

FIELD

The present technology is generally related to blood pumps, and, more particularly, to a method of determining a mean arterial pressure index in patients with an implantable blood pump.

BACKGROUND

Implantable blood pumps include a pumping mechanism to move blood from the heart to the rest of the body. For example, the pumping mechanism may be a centrifugal flow pump, such as the HVAD® Pump manufactured by HeartWare, Inc. in Miami Lakes, Fla., USA. In operation, the blood pump draws blood from a source, such as the right ventricle, left ventricle, right atrium, or left atrium of a patient's heart and impels the blood into an artery, such as the patient's ascending aorta or peripheral artery.

Typically, ill patients undergo Mean Arterial Pressure ("MAP") measurements in an effort to manage and prevent medical complications. MAP is generally defined as the average pressure in a patient's arteries during one cardiac cycle and may be obtained based on a patient's diastolic and systolic blood pressures. For patients having an implanted blood pump, however, it is often difficult to determine and/or estimate MAP, and MAP trends associated therewith, as a result of one or more hydraulic parameters external to the implanted blood pump being unknown.

SUMMARY

The techniques of this disclosure generally relate to a method of determining a mean arterial pressure index in patients with an implantable blood pump.

In one aspect, a method of determining a mean arterial pressure index of a patient having an implantable blood pump. The method includes determining a pump speed and a pump flow value. The pump speed and the pump flow value are analyzed in part with respect to a pump loss constant. A graft hydraulic resistance value is determined during a systolic phase of a cardiac cycle based on the analysis of the pump speed and the pump flow value with respect to the pump loss constant value. A mean arterial pressure index is determined during a diastolic phase of the cardiac cycle based on the determined graft hydraulic resistance value. The mean arterial pressure index of the patient is compared to a mean arterial pressure index range. An alert is generated when the mean arterial pressure index varies with respect to a mean arterial pressure index range.

In another aspect, analyzing the pump speed and the pump flow value to a pump loss constant value includes dividing the pump speed by the pump flow value and subtracting the pump loss constant value therefrom.

In another aspect, the method includes determining a ventricular pressure of the patient and analyzing the determined ventricular pressure of the patient relative to the graft hydraulic resistance value, the pump speed, the pump flow value and the pump loss constant value.

In another aspect, the method includes determining the ventricular pressure of the patient using a pressure sensor.

In another aspect, the method includes determining the ventricular pressure of the patient based on a ventricular pressure waveform estimation.

In another aspect, the pump loss constant value is associated with a pressure loss of the blood pump for a given pump flow.

In another aspect, the method includes establishing the mean arterial pressure index range based on the mean arterial pressure index measured during a plurality of time periods.

In one aspect, a method of determining a mean arterial pressure index of a patient having an implanted blood pump includes determining a graft hydraulic resistance value during a systolic phase of a cardiac cycle based on a pump speed, a pump flow value, and a pump loss constant value. The mean arterial pressure index is calculated during a diastolic phase of the cardiac cycle based on the graft hydraulic resistance value. A pump parameter adjustment is performed in response to the mean arterial pressure index deviating from a mean arterial pressure index range.

In another aspect, determining the graft hydraulic resistance value includes dividing the pump speed by the pump flow value and subtracting a pump loss constant value.

In another aspect, the method includes determining a ventricular pressure of the patient and analyzing the determined ventricular pressure of the patient relative to the graft hydraulic resistance value.

In another aspect, the method includes determining the ventricular pressure of the patient using at least one of a group consisting of a pressure sensor and a ventricular pressure waveform estimation.

In another aspect, the method includes performing a second pump parameter adjustment in response to the mean arterial pressure index deviating from the mean arterial pressure index range, the second pump parameter adjustment being different than the pump parameter adjustment.

In another aspect, the method includes executing a treatment response in response to the mean arterial pressure index deviating from the mean arterial pressure index range.

In another aspect, the graft hydraulic resistance value is external to the blood pump.

In another aspect, the method includes generating an alert in response to the mean arterial pressure index deviating from the mean arterial pressure index range.

In another aspect, the pump loss constant value is associated with a loss in pump pressure.

In one aspect, a system for determining a mean arterial pressure index of a patient having an implantable blood pump includes an implantable blood pump including an impeller. A controller is coupled to the blood pump and includes a control circuit configured to determine a graft hydraulic resistance value during a systolic phase of a cardiac cycle based on a pump speed, a pump flow value, and a pump loss constant value, calculate the mean arterial pressure index during a diastolic phase of the cardiac cycle based on the graft hydraulic resistance value, and perform a pump parameter adjustment in response to the mean arterial pressure index deviating from a mean arterial pressure index range.

In another aspect, the graft hydraulic resistance value is external to the blood pump.

In another aspect, the control circuit is configured to generate an alert in response to the mean arterial pressure index deviating from the mean arterial pressure index range.

In another aspect, the control circuit is configured to perform a second pump parameter adjustment in response to the mean arterial pressure index deviating from the mean arterial pressure index range, the second pump parameter adjustment being different than the pump parameter adjustment.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
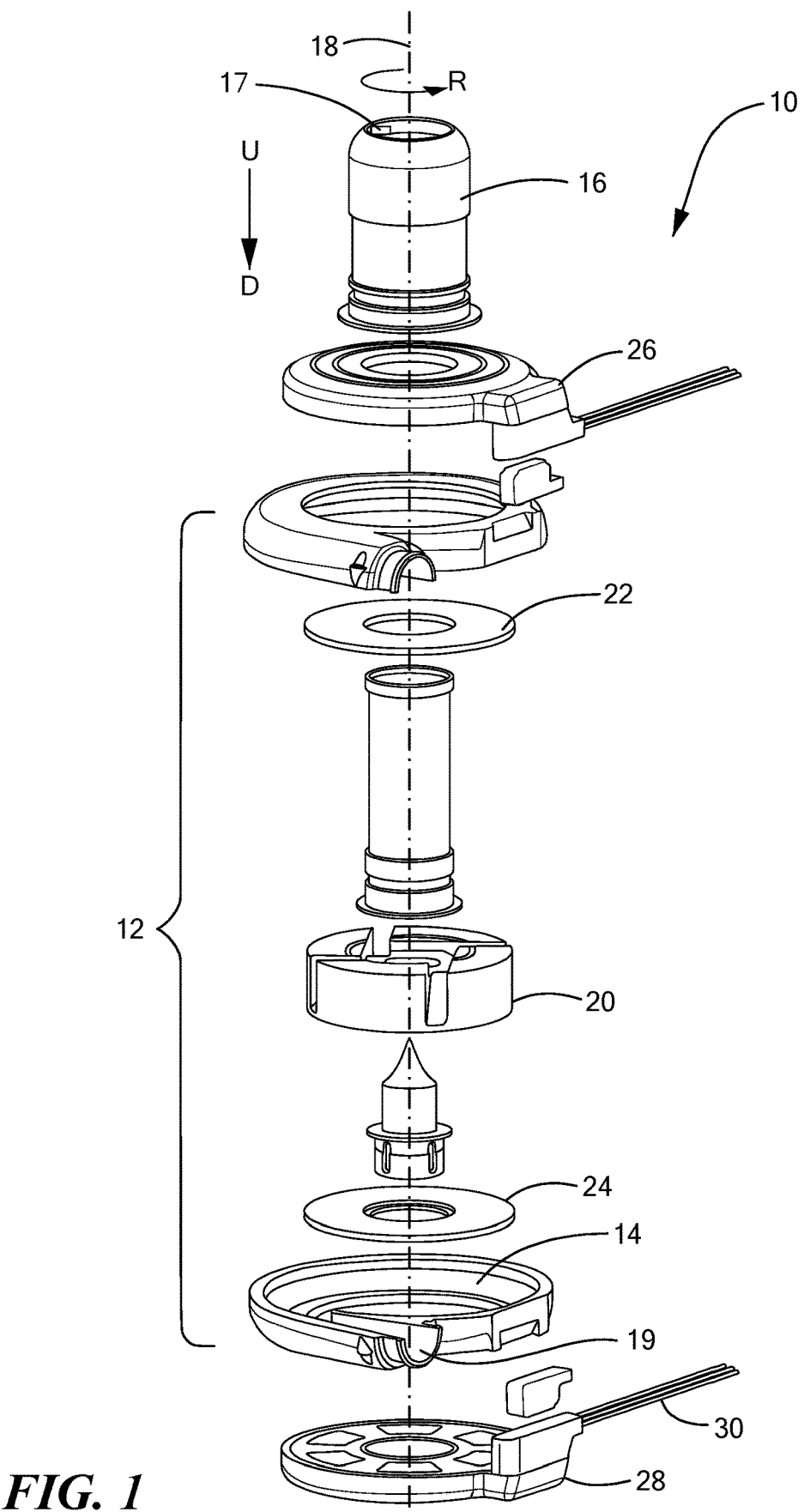
FIG. 1 is an exploded view of an exemplary blood pump constructed in accordance of the principles of the present invention.

Before describing in detail exemplary embodiments, it is noted that the embodiments reside primarily in combinations of device, system, and method steps related to determining a mean arterial pressure ("MAP") index in patients having an implanted blood pump. Accordingly, the device, system, and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Referring now to the drawings in which like reference designators refer to like elements there is shown in FIG. 1 a blood pump constructed in accordance with the principles of the present application and designated generally "10." The blood pump 10 is provided for illustrative purposes only as the methods of determining the MAP index described herein may be used with various types of blood pumps. The general arrangement of the blood pump components may be the same or similar to the HVAD® Pump described in U.S. Pat. Nos. 7,997,854 and 8,512,013, the disclosures of which are incorporated by reference herein in the entirety. For example, the blood pump 10 may include a housing 12 having a chamber 14, an inflow cannula 16 including a pressure sensor 17 coupled thereto, and a major longitudinal axis 18 extending through the inflow cannula. An enclosed flow path extends along the axis 18 from an upstream to a downstream direction, as indicated by the arrows U and D, respectively, from the inflow cannula 16 to a pump outlet 19. A generally disc-shaped ferromagnetic impeller 20 is mounted within the chamber 14 between a first ceramic disk 22 and a second ceramic disk 24 for rotation about the axis 18.

Figure 2:
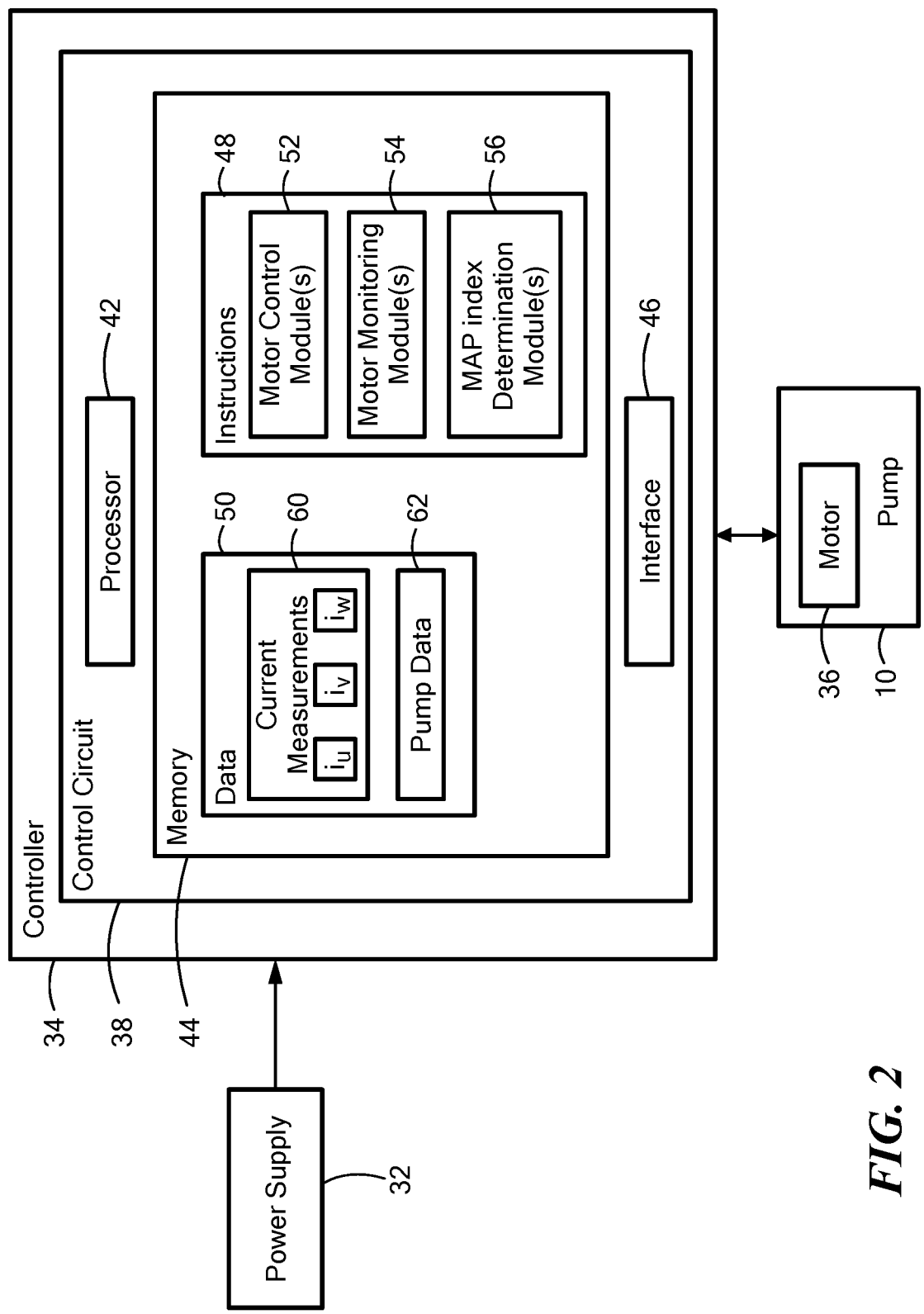
FIG. 2 is a block diagram of a power supply and a controller coupled to the blood pump of FIG. 1.

The blood pump 10 may be arranged so that the impeller 20 is levitated within the housing 12 by contactless bearings, such as magnetic bearings, hydrodynamic bearings or a combination of the two. For example, the blood pump 10 may include a first stator 26 and a second stator 28 disposed within the housing 12. The first stator 26 may be located proximate the first ceramic disk 22 and the second stator 28 may be located proximate the second ceramic disk 24. In operation, a voltage may be applied to one or more coils of the first stator 26 and/or the second stator 28 to rotate the impeller 20 to impel the blood. An electrical connector 30 may supply the voltage to the coils from, as shown in FIG. 2, a power supply 32 such as an external AC power supply, external battery, implanted battery, or any combination thereof, coupled to or stored within a controller 34. The blood pump 10, the power supply 32, and the controller 34 form a system for operating the blood pump 10 and determining a MAP index of the patient having the implanted blood pump 10.

With reference to FIGS. 1 and 2, the first stator 26 and the second stator 28 may operate in combination or independent of each other and may each form a portion of a sensorless three-phase brushless direct-current ("BLDC") motor 36. In one configuration, the coils of the first stator 26 and the second stator 28 are in the form of three motor windings controlled by a different respective phase U, V, W, of a power input for three-phase motor control. The BLDC motor includes an inverter circuit to convert a DC input to the three-phase output. Alternatively, the blood pump 10 may receive an alternating current (AC) three-phase input. Examples of three-phase motor control methods and devices are provided in commonly owned and co-pending U.S. Application Nos. 62/271,278, and Ser. No. 15/710,323, the disclosures of which are incorporated herein in the entirety.

FIG. 2 shows an example control circuit 38 coupled to the blood pump 10 including hardware and software for monitoring and controlling startup and subsequent operation of one or both of the motors 36. The control circuit 38 includes a processor 42, a memory 44, and an interface 46 for interfacing with the motor 36. The memory 44 stores information accessible by the processor 42, including instructions 48 that may be executed by the processor 42. The memory 44 also includes data 50 that may be retrieved, manipulated or stored by the processor 42. Further details associated with the control circuit 38 are provided in commonly owned and co-pending U.S. application Ser. No. 15/710,323, the disclosure of which is incorporated herein in the entirety.

The instructions 48 stored in the memory 44 may include one or more instruction sets or modules for performing certain operations in accordance with the present disclosure. For example, the modules may include a motor control module 52 for controlling operation of the motor 36, a monitor module 54 for monitoring operation of the motor 36, and/or a MAP index module 56 for executing a MAP index determination algorithm. Examples of motor control and monitoring modules may be found in commonly owned and copending U.S. application Ser. Nos. 13/355,297, 13/951,302, 14/294,448, 14/950,467, 62/266,871, and 62/271,618, the disclosures of which are incorporated herein by reference in their entireties. As understood by a person of ordinary skill in the art, MAP is used to determine whether there is adequate blood flow, pressure, and resistance to supply the blood to the patient's major organs.

Figure 3:
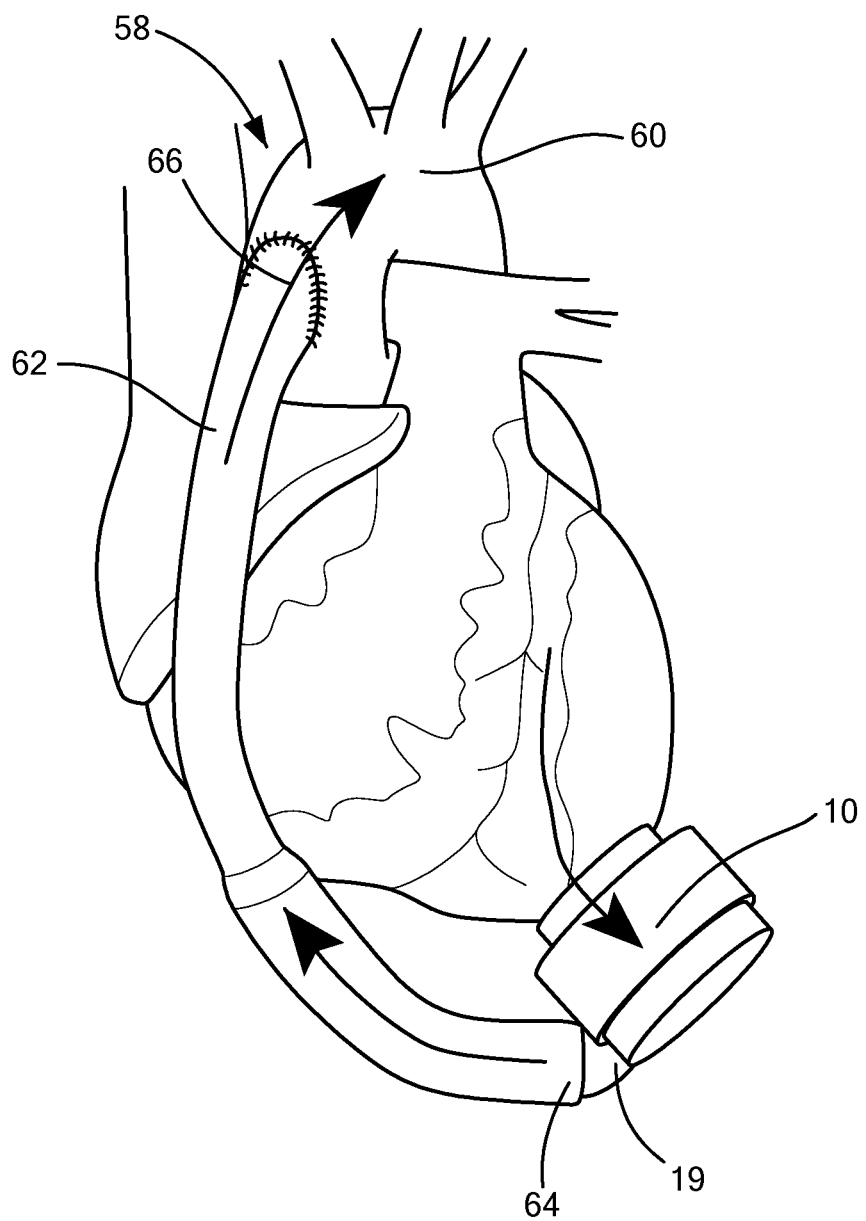
FIG. 3 is a perspective view of the blood pump of FIG. 1 implanted within a patient and coupled to a heart of the patient using a graft.

Referring now to FIG. 3, the blood pump 10 may be coupled to a patient's vascular system 58, such as an aorta 60, through a graft 62 in the form of a tube, cannula, or the like having a graft inlet 64 coupled to the pump outlet 19 and a graft outlet 66 coupled to the aorta 60. The graft 62 is a hydraulic resistance element which affects MAP but may be difficult to estimate or quantify as the graft 62 is implanted in the patient and external to the blood pump 10. For example, when the pump flow is circulating through the graft 62, there is a pressure drop across the graft 62 from the graft inlet 64 to the graft outlet 66 that affects MAP. As such, the MAP index determination algorithm accounts for the pressure drop, anastomosis, movement of the graft 62, the location and angle of the graft 62 with respect to the vascular system, and the like. In particular, the properties of the graft 62 are accounted for by determining a graft hydraulic resistance value based on an analysis of a pump speed, pump flow value, pump losses, and pump performance, as explained in further detail below.

Figure 4:
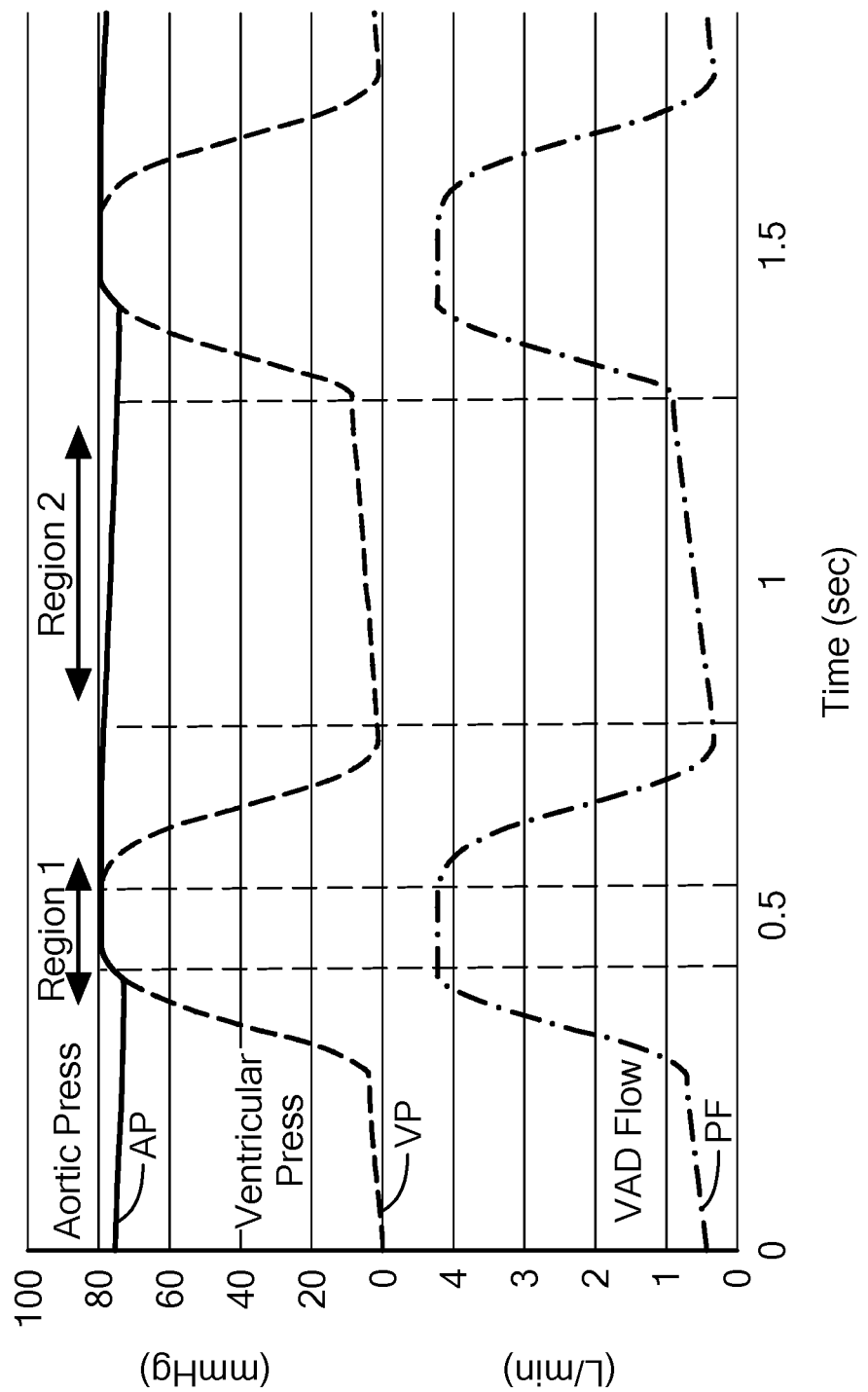
FIG. 4 is a graph displaying a flow waveform, a ventricular pressure waveform, and an aortic pressure waveform in accordance with the present invention.

Referring now to FIG. 4, a graph is depicted illustrating a pump flow waveform "PF," a ventricular pressure waveform "VP," and an aortic pressure waveform "AP," which provide data for determining the MAP index of the patient. The area designated as "Region 1" corresponds to a systolic phase of a cardiac cycle, whereas the area designated as "Region 2" corresponds to a diastolic phase of the cardiac cycle. The data from the waveforms within the systolic or diastolic phase may be input into the MAP index determination algorithm to determine the MAP index for the patient.

Figure 5:
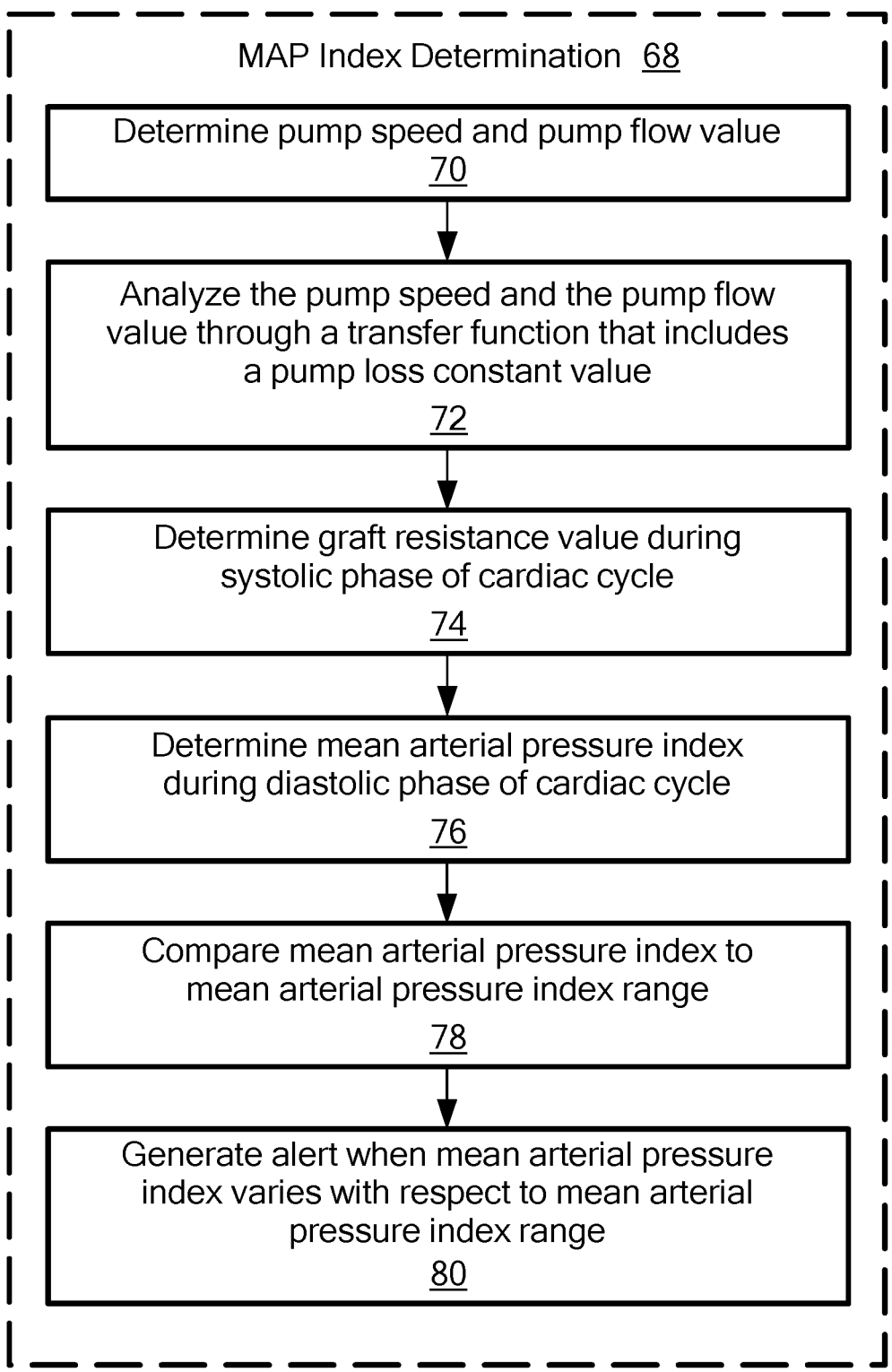
FIG. 5 is a flow diagram illustrating an exemplary method of determining a mean arterial pressure index of a patient having the blood pump implanted within the patient.

With reference to FIG. 5, a flow chart is provided depicting a process or method 68 of determining the MAP index of the patient having an implantable blood pump, such as the blood pump 10, implanted within the patient. The determined MAP index may be provided to a clinician for analyzing trends associated with changes in a patient's MAP. Such trends may assist in evaluating and providing treatments, adjusting pump parameters, and the like. The order of the method steps may vary and one or more steps may be added or omitted. The method may include continuously or periodically performing the MAP index algorithm through the control circuit 38 of the controller 34 (FIG. 2) with the algorithm based on a graft resistance value and data from the pump flow waveform (FIG. 4) independent of preload pressure. For example, the method may be repeated in various intervals, such as 5 to 50 seconds for at least one minute, every 15 to 20 minutes, or another series of intervals.

In one configuration, the method 68 begins at step 70 including determining the pump speed and the pump flow value for the blood pump 10. For example, and without limitation, the pump speed may be determined from the control circuit 38 and the pump flow value may be determined based on the current, the pump speed, and the viscosity of the blood. As shown in FIG. 4, the pump flow value may be displayed in real time via the pump flow waveform indicating the pump flow rate through the blood pump 10. Alternative methods of determining the pump parameters are within the scope of the disclosure.

Step 72 includes processing the pump speed and the pump flow value through a transfer function that includes a pump loss constant value, with the pump loss constant value being a predetermined pressure constant associated with a known pressure loss specific to the blood pump 10.

At step 74, the method includes determining the graft hydraulic resistance value during the systolic phase of the cardiac cycle, i.e., Region 1 of FIG. 4, based on the analysis of the pump speed and the pump flow value, pump hydraulic output, and the pump loss constant value. The graft hydraulic resistance value includes the properties of the graft and hydraulic resistance discussed above. In terms of the algorithm, the analysis for determining the graft hydraulic resistance value may appear as $$Rg = \frac{Ho(\text{Speed})}{Q^2_{sys\_max}} - Kp$$

where Ho(Speed) is the pump's shutoff pressure output at a given Speed and approximated by $$Ho(\text{Speed}) \approx \left(\frac{\text{Speed}}{So}\right)^2$$

where So is a pump scaling constant related to the pump's shutoff pressure at a given Speed (Region 1), Rg equals the graft hydraulic resistance value, Q equals the pump flow value, and Kp equals the pump loss constant value.

At step 76, the method includes determining the MAP index during the diastolic phase of the cardiac cycle, i.e., Region 2 of FIG. 4, when an aortic valve of the patient is closed based on the determined graft resistance value, as well as the pump speed, the pump loss constant value, and the pump flow value. The MAP index algorithm may be expressed as MAP2=Ho(Speed)−((Kp+Rg$_{est}$) Q$^2_{dias}$) where MAP2 equals the MAP index. The MAP index may be displayed in various forms such as a waveform on the display of the controller 34 or a remote display (not shown) with or without filtering.

Once the MAP index is determined, the method may proceed to step 78 including comparing the MAP index of the patient to a MAP index range. The MAP index range is a range in which the MAP index of the patient is considered to be normal for the individual patient taking into account the time of day, activity of the patient, etc. The comparison between the MAP index and the MAP index range may be executed by the control circuit 38 or another control circuit remote from the patient.

At step 80, the control circuit 38 or the control circuit in the remote location generates an alert when the MAP index varies with respect to, i.e., outside of, the MAP index range. The alert may be audible through a speaker (not shown), visual through a display (not shown) of the controller 34, a remote display, or the like. Thus, the deviation in the MAP index with respect to the MAP index range may signify a need for and result in a diagnostic intervention or therapeutic treatment. For example, the MAP index deviation may result in a clinician or other treatment provider performing a pump parameter adjustment, such as a speed adjustment, which affects the pump flow to raise or lower the patient's blood pressure. A second pump parameter adjustment may be performed which is different than the pump parameter adjustment, such as adjusting a hematocrit setting of the controller 34 in accordance with hematocrit changes. In another example, the clinician may execute a treatment response, such as prescribing one or more medications depending upon the data provided by the MAP index. To further assist in evaluating diagnostic intervention and/or treatment plans, the control circuit 38 may generate one or more MAP index reports indicating the changes in the MAP index over select time periods, such as days, weeks, months, etc.

In one configuration, the method may include determining a ventricular pressure of the patient, i.e. the pressure in the patient's left ventricle based on the pressure sensor 17 (FIG. 1) or based on a ventricular pressure waveform estimation. Thereafter, the method may proceed with analyzing the determined ventricular pressure of the patient relative to the graft resistance value, the pump speed, the pump flow value and the pump loss constant value. In terms of an algorithm, such determination may appear as $$P_{Vent} + H_{so}(\text{Speed}) - K_p Q^2 - R_g Q^2 - L_g \frac{dQ}{dt} = P_{aorta}$$

where P$_{aorta}$ equals the pressure in the aorta which is indicative of MAP.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of determining a mean arterial pressure index of a patient having a blood pump, the method comprising:
   determining a graft hydraulic resistance value during a systolic phase of a cardiac cycle of the patient based on a pump speed, a pump flow value, and a pump loss constant value of the blood pump;
   calculating the mean arterial pressure index during a diastolic phase of the cardiac cycle based on the graft hydraulic resistance value; and
   adjusting a pump parameter of the blood pump in response to the mean arterial pressure index deviating from a mean arterial pressure index range.

2. The method of claim 1, further comprising determining a ventricular pressure of the patient and analyzing the determined ventricular pressure of the patient relative to the graft hydraulic resistance value.

3. The method of claim 1, wherein the graft hydraulic resistance value is external to the blood pump.

4. The method of claim 1, further comprising generating an alert in response to the mean arterial pressure index deviating from the mean arterial pressure index range.

5. A system comprising:
   an implantable blood pump including an impeller; and
   a controller coupled to the blood pump and including a control circuit configured to:
     determine a graft hydraulic resistance value during a systolic phase of a cardiac cycle of a patient based on a pump speed, a pump flow value, and a pump loss constant value of a blood pump;
     calculate the mean arterial pressure index during a diastolic phase of the cardiac cycle based on the graft hydraulic resistance value; and
     perform a pump parameter adjustment related to the implantable blood pump in response to the mean arterial pressure index deviating from a mean arterial pressure index range.

6. The system of claim 5, wherein the graft hydraulic resistance value is external to the blood pump.

7. The system of claim 5, wherein the control circuit is configured to generate an alert in response to the mean arterial pressure index deviating from the mean arterial pressure index range.

8. The system of claim 5, wherein the control circuit is configured to perform a second pump parameter adjustment in response to the mean arterial pressure index deviating from the mean arterial pressure index range, the second pump parameter adjustment being different than the pump parameter adjustment.

9. The system of claim 5, wherein to determine the graft hydraulic resistance value, the control circuit is configured to divide the pump speed by the pump flow value and subtract the pump loss constant value.

10. The system of claim 5, wherein the control circuit is configured to determine a ventricular pressure of the patient and analyze the determined ventricular pressure of the patient relative to the graft hydraulic resistance value.

11. The system of claim 10, wherein the control circuit is configured to determine the ventricular pressure of the patient using at least one of a pressure sensor or a ventricular pressure waveform estimation.

12. The system of claim 5, wherein the control circuit is configured to execute a treatment response in response to the mean arterial pressure index deviating from the mean arterial pressure index range.

13. The system of claim 5, wherein the pump loss constant value is associated with a loss in pump pressure.

14. A system comprising:
a blood pump including an impeller;
a controller including a control circuit configured to:
determine a pump speed and a pump flow value of the blood pump;
analyze the pump speed and the pump flow value at least in part with respect to a pump loss constant value;
determine a graft hydraulic resistance value during a systolic phase of a cardiac cycle of a patient based on the analysis of the pump speed and the pump flow value with respect to the pump loss constant value;
determine a mean arterial pressure index during a diastolic phase of the cardiac cycle based on the determined graft hydraulic resistance value;
compare the mean arterial pressure index of the patient to a mean arterial pressure index range; and
generate an alert in response to determining the mean arterial pressure index varies with respect to a mean arterial pressure index range.

15. The system of claim 14, wherein to analyze the pump speed and the pump flow value to the pump loss constant value, the control circuit is configured to divide the pump speed by the pump flow value and subtract the pump loss constant value.

16. The system of claim 14, wherein the control circuit is configured to determine a ventricular pressure of the patient and analyze the determined ventricular pressure of the patient relative to the graft hydraulic resistance value, the pump speed, the pump flow value, and the pump loss constant value.

17. The system of claim 16, wherein the control circuit is configured to determine the ventricular pressure of the patient using a pressure sensor.

18. The system of claim 16, wherein the control circuit is configured to determine the ventricular pressure of the patient based on a ventricular pressure waveform estimation.

19. The system of claim 14, wherein the pump loss constant value is associated with a pressure loss of the blood pump.

20. The system of claim 14, wherein the control circuit is configured to establish the mean arterial pressure index range based on the mean arterial pressure index measured during a plurality of time periods.

* * * * *